(12) United States Patent
Brink et al.

(10) Patent No.: US 7,043,989 B2
(45) Date of Patent: May 16, 2006

(54) METHOD AND APPARATUS FOR TESTING INSTALLATION QUALITY IN A GROUTED ANCHOR SYSTEM

(75) Inventors: Van Zyl Brink, Gauteng (ZA); Ismet Canbulat, Gauteng (ZA); Johann Haarhoff, Gauteng (ZA)

(73) Assignee: CSIR, Pretoria (ZA)

( * ) Notice: Subject to any disclaimer, the term of this patent is extended or adjusted under 35 U.S.C. 154(b) by 41 days.

(21) Appl. No.: 10/880,074

(22) Filed: Jun. 29, 2004

(65) Prior Publication Data

US 2005/0011265 A1    Jan. 20, 2005

(30) Foreign Application Priority Data

Jun. 30, 2003  (ZA)  ................. 2003/5080

(51) Int. Cl.
*G01N 29/04* (2006.01)

(52) U.S. Cl. .............................. 73/579; 73/594; 73/582

(58) Field of Classification Search .......... 73/573–574, 73/577, 579, 582, 584, 585, 587, 588, 594
See application file for complete search history.

(56) References Cited

U.S. PATENT DOCUMENTS

| 5,457,994 A | * | 10/1995 | Kwun et al. ................. 73/587 |
| 5,798,981 A | * | 8/1998 | Littlejohn et al. ............ 367/13 |
| 5,821,430 A | * | 10/1998 | Kwun et al. ............. 73/862.41 |
| 6,109,109 A | * | 8/2000 | Brown ........................ 73/632 |
| 6,422,079 B1 | * | 7/2002 | Rodger et al. ................ 73/579 |

FOREIGN PATENT DOCUMENTS

JP          2003-315214    * 11/2003

OTHER PUBLICATIONS

James L. Withiam, et al., NCHRP (National Cooperative Highway Research Program), Report 477, entitled "Recommended Practice for Evaluation of Metal-Tensioned Systems In Geotechnical Applications", 2002.

D'Appolonia, McMahon & Mann, NCHRP (National Cooperative Highway Research Program), Web Document 27 Entitled Evaluation of Metal-Tensioned Systems in Geotechnical Applications, Phase 1—Interim Report, Mar. 2001.

A.M. Kelly and A.J. Jager, SIMRAC (Safety in Mines Research Advisory Committee) Final Project Report Entitled "Critically Evaluate Techniques for the In Situ Testing of Steel Tendon Grouting Effectiveness as a Basis for Reducing Fall of Ground Injuries and Fatalities", Oct. 1996.

Johann Haarhoff, Literature Review for In Situ Bolt Integrity Tester, which summarizes a review of the literature conducted by the inventors Haarhoff and Canbulat, no date.

* cited by examiner

*Primary Examiner*—Helen Kwok
(74) *Attorney, Agent, or Firm*—Frommer Lawrence & Haug LLP; Ronald R. Santucci

(57) ABSTRACT

The invention concerns a method of testing the installation quality of a grouted anchor system comprising at least one tendon anchored by grout in a hole in a surrounding mass. The system typically includes a group of roof bolts (10, 12) each having a tendon (10.1, 10.2) anchored in a rock mass (22) by grout (14, 16). The method includes the steps of applying an acoustic signal to the system, detecting the acoustic response(s) of the tendon(s) and assessing the installation quality of the tendon(s) from an analysis of such response(s). The invention also includes apparatus for use in the method.

15 Claims, 7 Drawing Sheets

METHOD AND APPARATUS FOR TESTING INSTALLATION QUALITY IN A GROUTED ANCHOR SYSTEM

This application claims priority benefits from South African Patent Application No. 2003/5080 filed Jun. 30, 2003.

BACKGROUND TO THE INVENTION

THIS invention relates to a method and apparatus for testing installation quality in a grouted anchor system.

The invention is particularly, but not solely concerned, with so-called "metal tensioned systems". The term "metal tensioned system" is used in this specification to refer to the class of products which includes prestressed ground or rock anchors and rock bolts, sometimes referred to as "roof bolts", of both bar and strand type. Products of this type have been in widespread use for many years in civil engineering and mining applications, in the latter case typically for the purposes of roof support and consolidation.

A metal tensioned system has a tendon of bar or strand form which is anchored in a predrilled hole by a mechanical anchorage or grout and subsequently tensioned. The present invention is particularly concerned with grout-type systems making use of resin or cement grouts. In such systems, it will be understood that the performance of the metal tensioned system is largely dependent on the quality of the grout used to anchor the tendon and hence the bonding of the tendon to the material in which the hole is drilled. Poor performance may, for example, result from poor or non-uniform grout application, insufficient quantity of grout or poor mixing of the grout. Simple visual inspection of the protruding end of the metal tensioned system usually provides little or no true indication of the condition or quality of the installation and in particular the quality of the grout. To address this problem a number of non-destructive testing methods have been proposed to test the installation quality of the grouted system. Such methods have included acoustic testing, electrochemical testing and magnetic flux leakage testing. Of the known methods, the acoustic methods have proved to be the most promising.

One known device for implementing an acoustic technique is known as the Boltometer. In the use of this technique an ultrasonic pulse is applied to the protruding end of a metal tensioned system under test, and the magnitude of the echo signal reflected in that system is measured. From these measurements, a skilled person can theoretically obtain an indication of the quality of the installation.

The Boltometer technique does however have several serious shortcomings. One of these is the inability of the technique to analyse grout quality in strand or cable-type metal tensioned systems, or in non-linear metal tensioned systems such as "Shepherd's Crook"—type systems. Other shortcomings are the necessity to grind the protruding end of the tendon flat in order for testing to take place, the necessity to calibrate the apparatus for the particular tendon and rock type under consideration and the necessity for an acoustic coupling between the Boltometer transducer and the tendon. Given that the acoustic system is applied to the tendon in the vicinity of this coupling, the coupling must be appropriately resistant to the applied signal.

Another known, somewhat similar testing technique is that proposed by the National Cooperative Highway Research Project (NCHRP). In this technique, an impact is applied to, for instance, the protruding end of a rock or roof bolt under test and the reflected frequency spectrum for that bolt is monitored and used to provide an indication of the installation quality of the grout of that bolt.

This technique also has its shortcomings, notably a necessity to grind the end of the tendon flat to enable an accelerometer to be attached and the fact that the tendon diameter must in general be at least 25 mm. In mining applications, tendons of such large diameter are seldom used, so the NCHRP technique is of limited value in such applications. Also, there is a necessity for the accelerometer coupling to be impact resistant.

It is an object of the present invention to provide a method and apparatus which addresses the above-noted disadvantages of the known Boltometer and NCHRP techniques.

SUMMARY OF THE INVENTION

According to the invention there is provided a method of testing the installation quality of a grouted anchor system comprising at least one tendon anchored by grout in a hole in a surrounding mass, the method including the steps of applying an acoustic signal to the system, detecting the acoustic response(s) of the tendon(s) and assessing the installation quality of the tendon(s) from an analysis of such response(s).

The term "acoustic signal" is used in this specification to refer to a vibratory signal which is not necessarily in the audible range. Typically the signal is applied by impacting the protruding end of the tendon, or some of them if there is a plurality of tendons, but it could also be applied by impacting any other part of the system such as the material, typically rock, in which the tendon(s) is or are anchored by the grout. It is feasible for the signal and response(s) to be generated by a single impact only, but in practice it is preferred that there be a series of periodic impacts.

The term "grout" and related terms such as "grouted" apply to both cementitious and resin type grouts.

The invention may in one important application be used to test the installation quality of a group of rock or roof bolts anchored by grout in a rock mass. In a simple form of the invention, the signal is applied to the end of a tendon in respect of which it is known that the installation quality is good and which is to serve as a reference tendon, and the response(s) of the other tendons are detected and compared. Alternatively for each comparison of one tendon response with another tendon response, a function is derived which can be applied to the one response to equalise it with the other response and the totality of the derived functions is analysed to give an indication of the installation quality of the tendons of the bolts in the group as a whole.

The invention also provides apparatus for testing the installation quality of a grouted anchor system comprising at least one tendon anchored by grout in a hole in a surrounding mass, the apparatus including means for applying an acoustic signal to the system and means for detecting the acoustic response(s) of the tendon(s), whereby an assessment of the installation quality of the system can be derived from an analysis of such response(s).

BRIEF DESCRIPTION OF THE DRAWINGS

The invention will now be described in more detail, by way of example only, with reference to the accompanying drawings in which.

SPECIFIC DESCRIPTION

Figure 1:
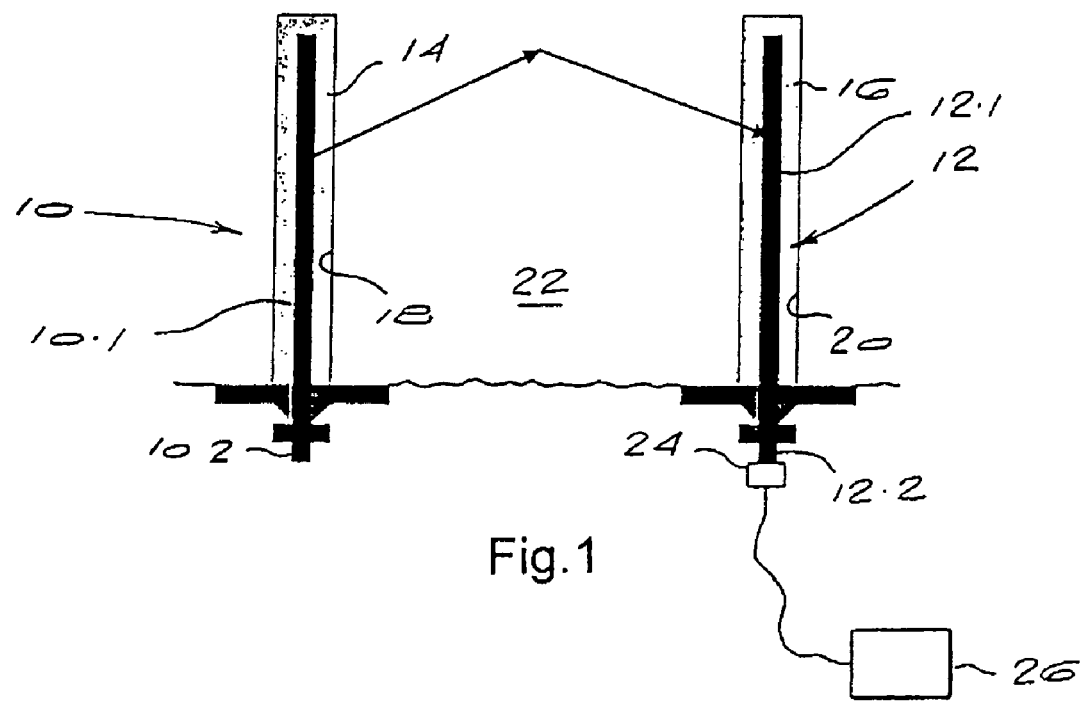
FIG. 1 illustrates, in a simplified cross-sectional view, an underlying principle of the invention.
Figure 2:
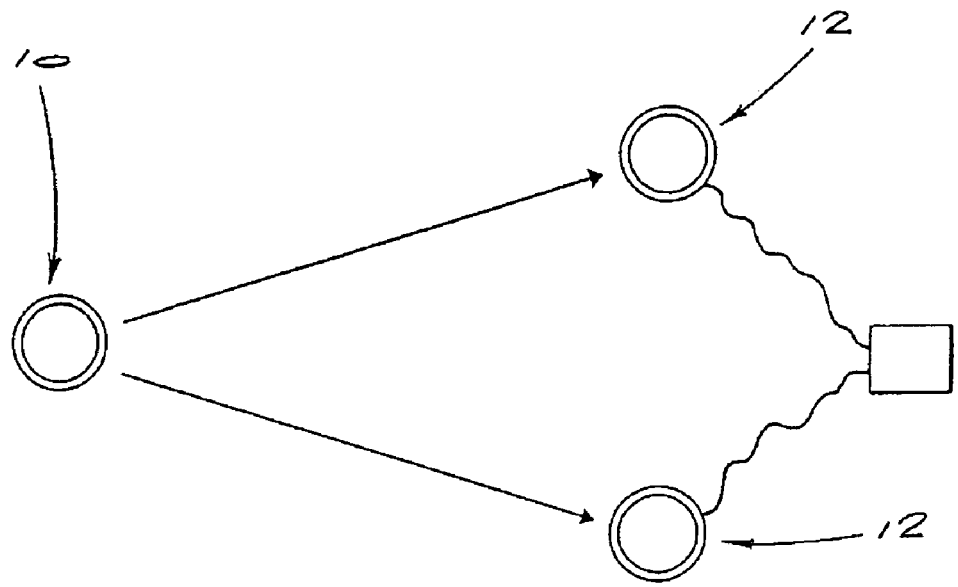
FIG. 2 illustrates the same principle in a simplified view, from below, on the roof of a mine working in which roof bolts have been installed.

The underlying principle of the invention is explained with reference to FIGS. 1 to 6 of the accompanying drawings. FIGS. 1 and 2 diagrammatically illustrate a grouted metal tensioned system which comprises a first roof bolt 10, referred to as a reference bolt, having a tendon 10.1 and two second roof bolts 12, referred to as test bolts, which have tendons 12.1 and which are spaced apart from one another and from the reference bolt 10. The bolts 10 and 12 are anchored by grout 14, 16 in predrilled holes 18, 20 in a rock mass 22.

In this explanatory example, the installation quality of the bolt 10 is known to be good. This implies that grout 14 of the correct quality has been used in the correct quantity and in accordance with correct, predetermined procedures to anchor the tendon 10.1 in the hole 18 in the rock mass 22. The quality of installation of the bolts 12 is unknown, i.e. it is not known whether the correct quantity or quality of grout 16 has been used or whether correct grouting procedures, for example in terms of mixing, have been followed.

An acoustic signal is applied to the protruding end 10.2 of the tendon 10.1 of the reference bolt 10 by means of a suitable impact device, typically a hammer or the like. As indicated by the arrows in FIG. 1 the signal travels through the tendon 10.1, grout 14, rock mass 22, grout 16 and tendons 12.1.

The signal which reaches the protruding ends 12.2 of the tendons 12.1 is picked up by respective transducers 24, typically in form of a microphones or geophones, which convey the signal in electrical form to a processor 26 which analyses the signal and produces corresponding frequency spectra. The processor may, for instance, incorporate a graphic equalizer and accompanying data logger, although other techniques for manipulating the received signal, typically in digital form, are within the scope of the invention.

It will be understood that in the course of its travel from the bolt 10 to the bolts 12 through the rock mass, the signal will be attenuated, reflected and otherwise affected to some extent by faults, parting planes and the like in the intervening rock mass and that the detected signals at the tendons 12.1 will be affected accordingly. However it is also recognised that in a practical application where a grouted metal tensioned system is installed in, say, the hanging wall or roof of a coal mine working, it is generally true that the intervening rock mass is largely homogeneous, implying that distortions of the signal attributable to localised variations in the rock mass will be minimal and can largely be ignored.

From the point of view of the present invention, a more important variable affecting the signals received at the ends 12.2 of the tendons 12.1 is the quality of the grout 16 which secures the tendons 12.1 of the bolts 12 in the rock mass 22. In this regard it is important to recognise that it is, in the case of any grouted metal tensioned system, the grout which couples the tendons of the system acoustically to the surrounding mass. Where the grout quality is poor, for instance because of voids or discontinuities therein or improper mixing thereof, there will be poor acoustic coupling with the surrounding mass and accordingly a variation between the signals received in such situations compared to situations where the grout quality is good and the acoustic coupling is correspondingly good. This is illustrated in FIGS. 3 to 6 which graphically illustrate frequency spectra for tests conducted on a laboratory scale.

Figure 3:
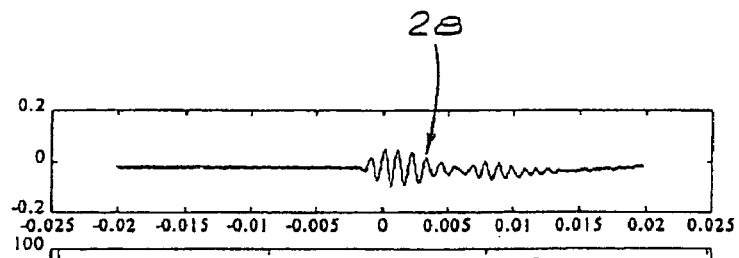
FIGS. 3 to 6 graphically illustrate test results for bolts for which the quality of installation is good and poor respectively.
Figure 4:
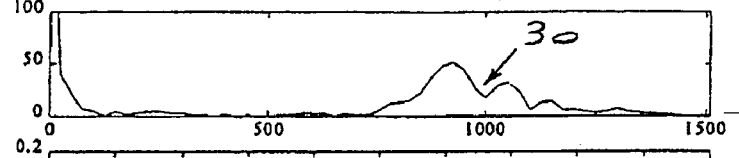

FIG. 3 depicts an acoustic signal received at the end of a roof bolt where the installation quality is good. Signal intensity or amplitude is shown on the vertical axis and time on the horizontal axis. Such a spectrum might, for example, be obtained from a bolt having an installation quality similar to that of the bolt 10. The acoustic signal received at the end of the tendon of such a bolt is clearly indicated in the region 28 of the graph. FIG. 4 shows a corresponding frequency spectrum for the same bolt. The frequency spectrum attributable to the impact applied to the remote bolt is clearly indicated in the corresponding region 30 of this graph.

Figure 5:
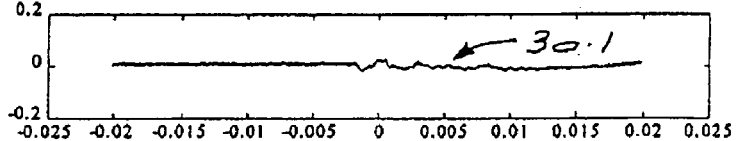
Figure 6:
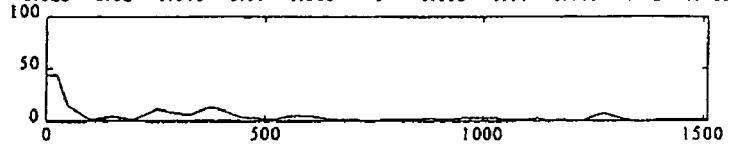

FIGS. 5 and 6 show graphs corresponding to the graphs of FIGS. 3 and 4 for a bolt 12 where the grout quality is poor, in this case because only a single capsule of resin grout, as opposed to the two capsules specified for the installation in question, was used. It will be noted that although the acoustic signal is detected in the time region 28.1 corresponding to the region 28 in FIG. 3, the intensity thereof is greatly diminished compared to FIG. 3. From FIG. 4 it is seen that there is little or no correlation between the detected frequency spectrum and that obtained for the "good" bolt.

Figure 7:
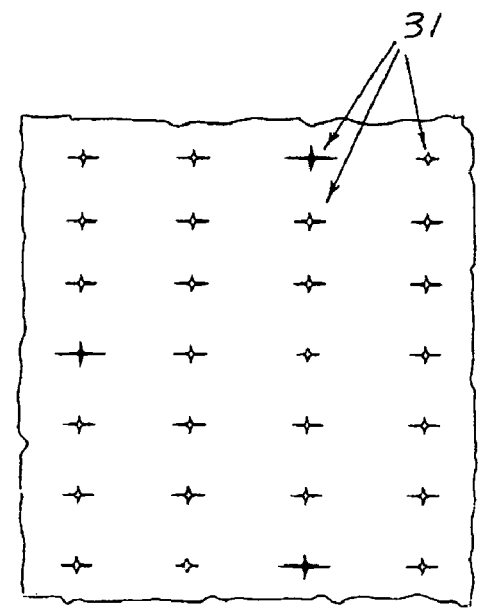
FIG. 7 diagrammatically illustrates the roof a mine working in which a group of bolts which are to be tested have been installed, FIGS. 8 to 13 graphically illustrate test results obtained from an array of bolts as illustrated in FIG. 7.

FIG. 7 shows a view looking upwardly onto a roof in a coal mine where roof bolts 31 have been installed in a predetermined, regular pattern for test purposes. Some of the bolts are "good" bolts, i.e have been installed correctly while the remaining bolts are "bad" bolts which have poor quality installation as a result of undermixing of the grout, overmixing of the grout, lack of proper bolt tension, overdrilling of the hole (i.e. the hole is too long in relation to the tendon 12.1), expiration of the grout, (i.e. deterioration of the grout through passage of time, or use of insufficient grout (i.e. use of a single grout capsule instead of the required two capsules). FIGS. 8 to 13 graphically illustrate the test results obtained.

In the tests, multiple, periodic impacts were applied to a selected one of the bolts and the signals introduced into the relevant bolt were normalised. The signals detected at the other bolts were added and averaged according to their quality of installation, i.e. the signals received at those bolts of inferior installation quality as a result of undermixing were added and averaged, those received at bolts of inferior installation quality as a result of overmixing were added and averaged, and so on.

Figure 8:
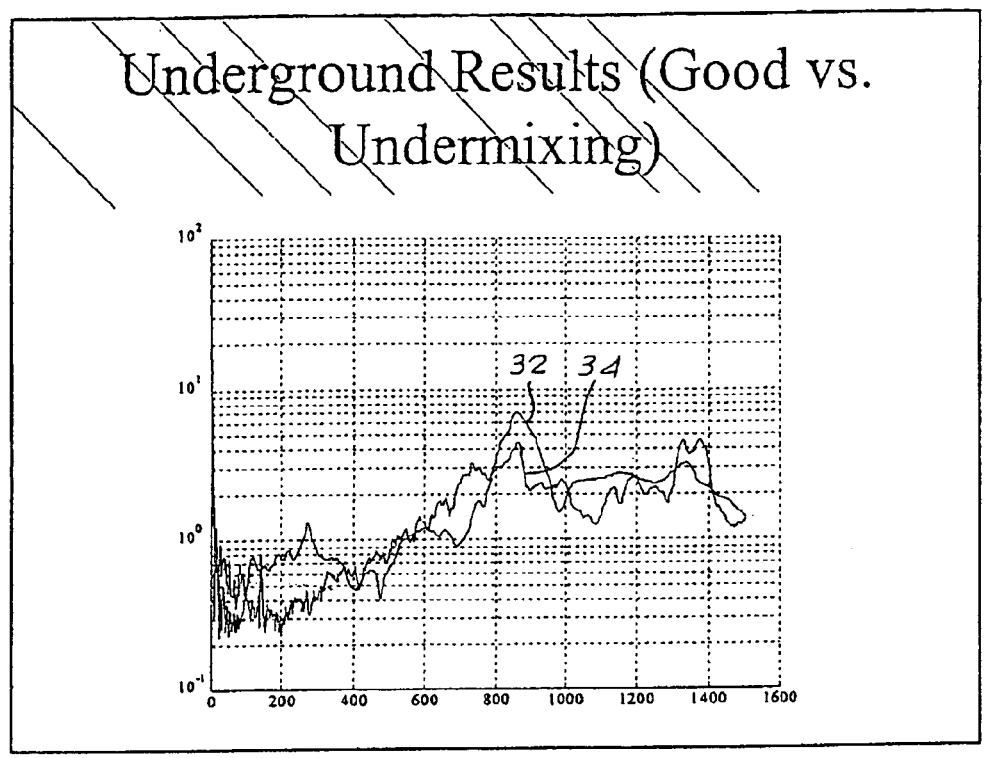

In FIG. 8, the numeral 32 indicates the detected frequency spectrum for a "good" bolt and the numeral 34 the corresponding spectrum for a bolt where there was undermixing of the grout components during installation. The marked differences between the two spectra are readily visible.

Figure 9:
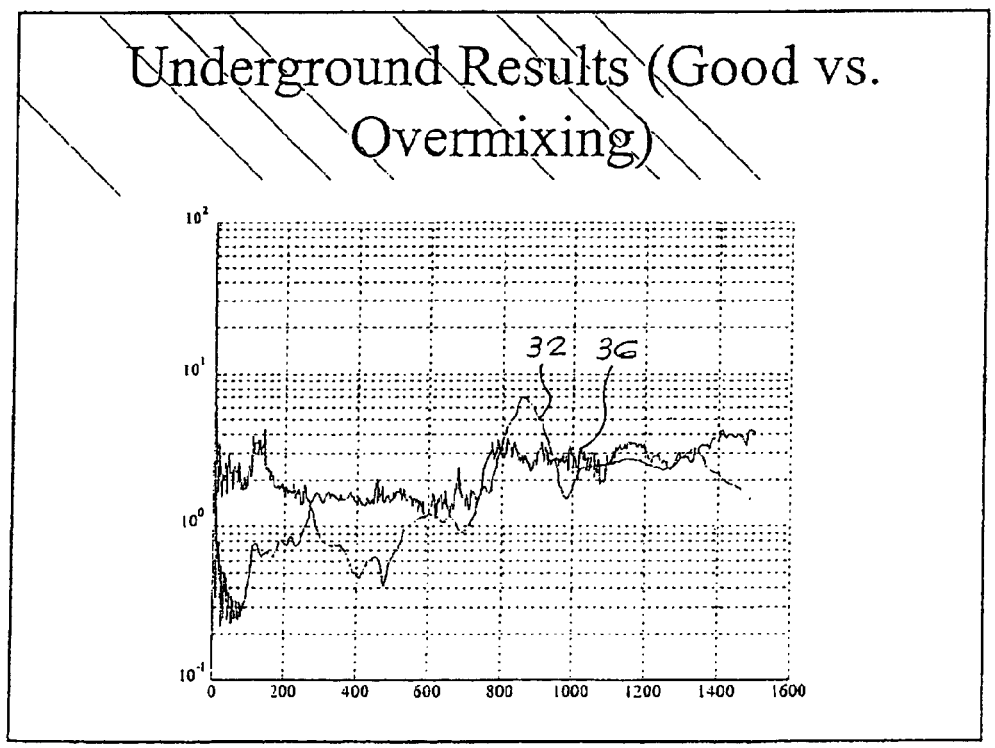

FIG. 9 shows the marked difference between the same spectrum 32 and the spectrum 36 obtained for a bolt where the grout was overmixed during installation.

Figure 10:
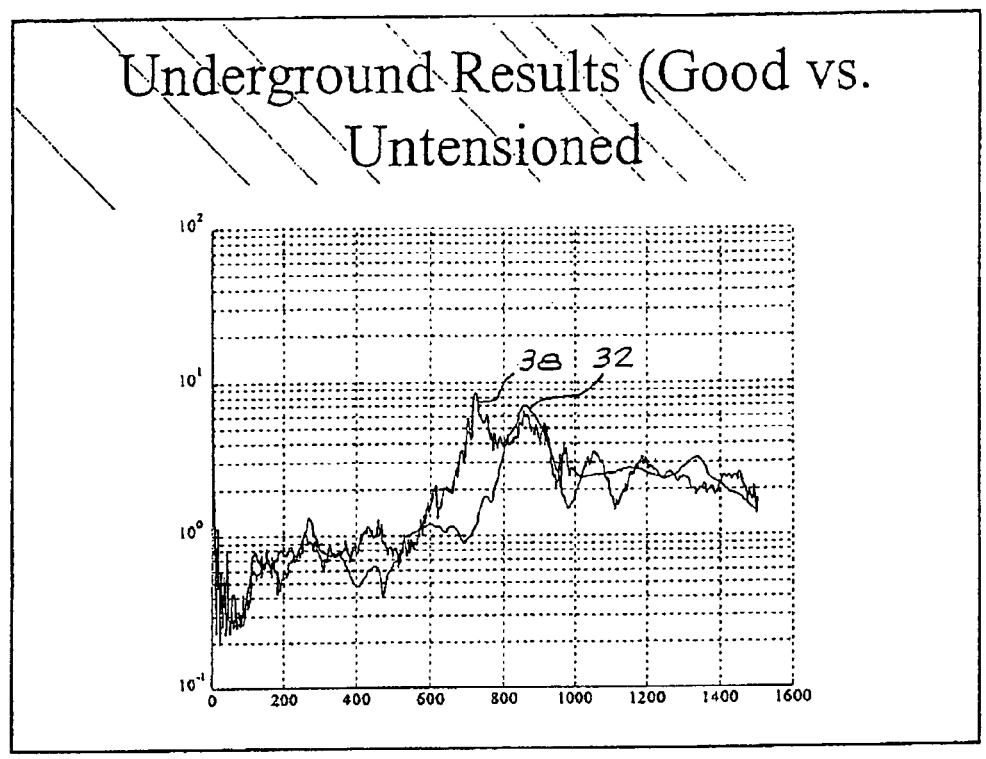

FIG. 10 shows the marked difference between the spectrum 32 and the spectrum 38 obtained for a bolt where the installation quality is poor as a result of failure to tension the roof bolt.

Figure 11:
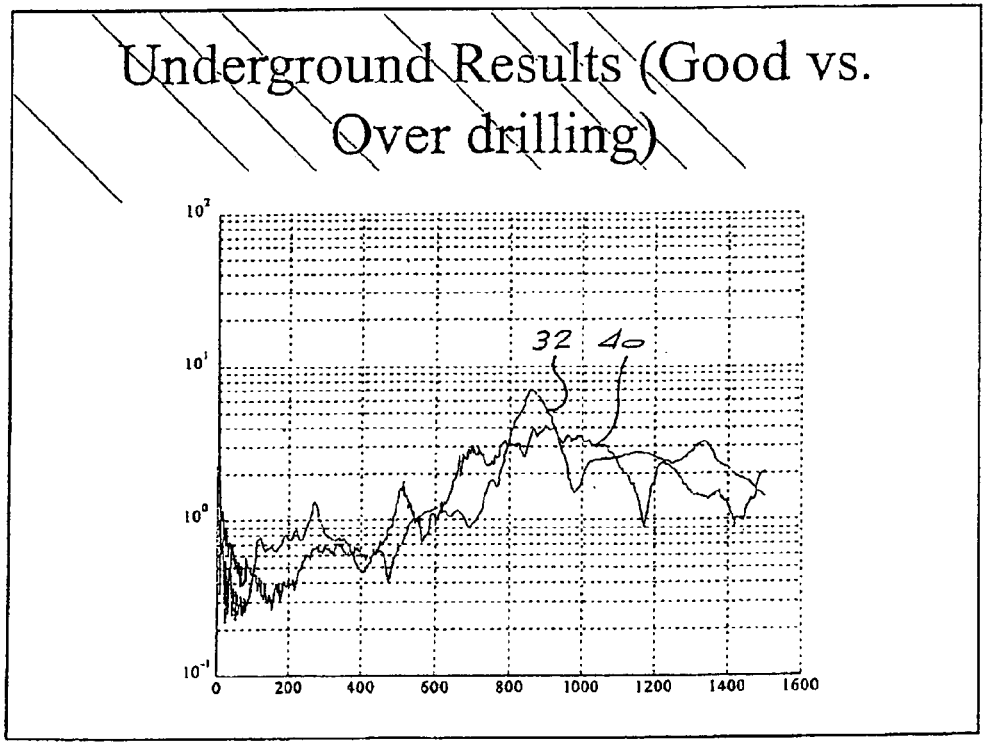

FIG. 11 shows the marked difference between the spectrum 32 and the spectrum 40 obtained for a bolt where the installation quality is poor as a result of overdrilling of the hole.

Figure 12:
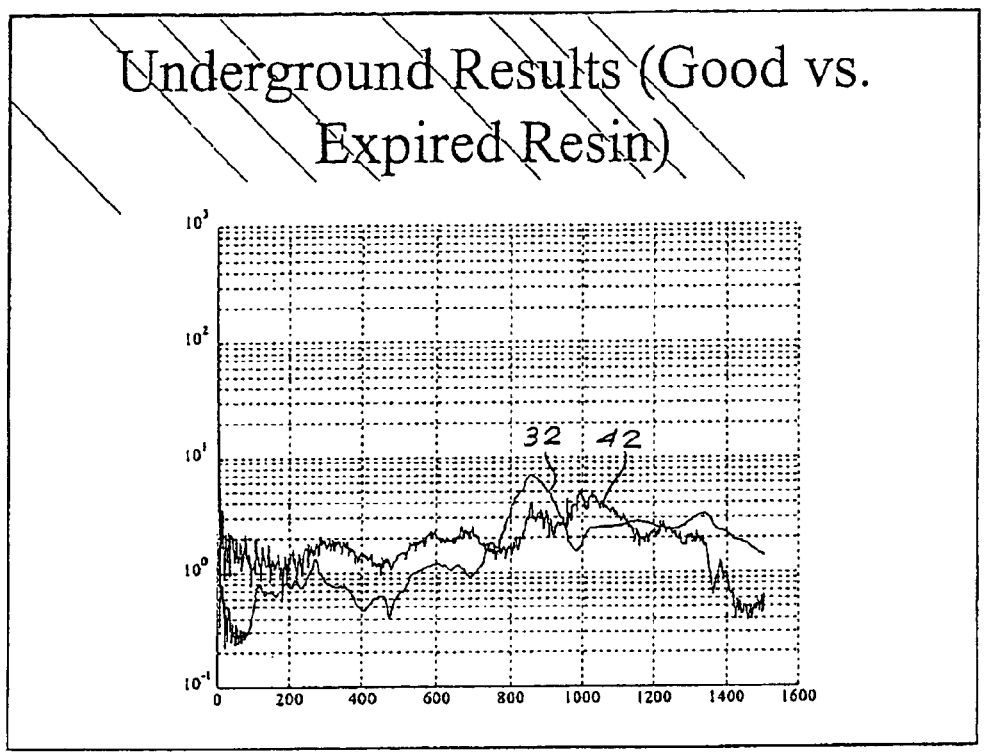

FIG. 12 shows the marked difference between the spectrum 32 and the spectrum 42 obtained for a bolt where the installation quality is poor as a result of the use of expired grout resin.

Figure 13:
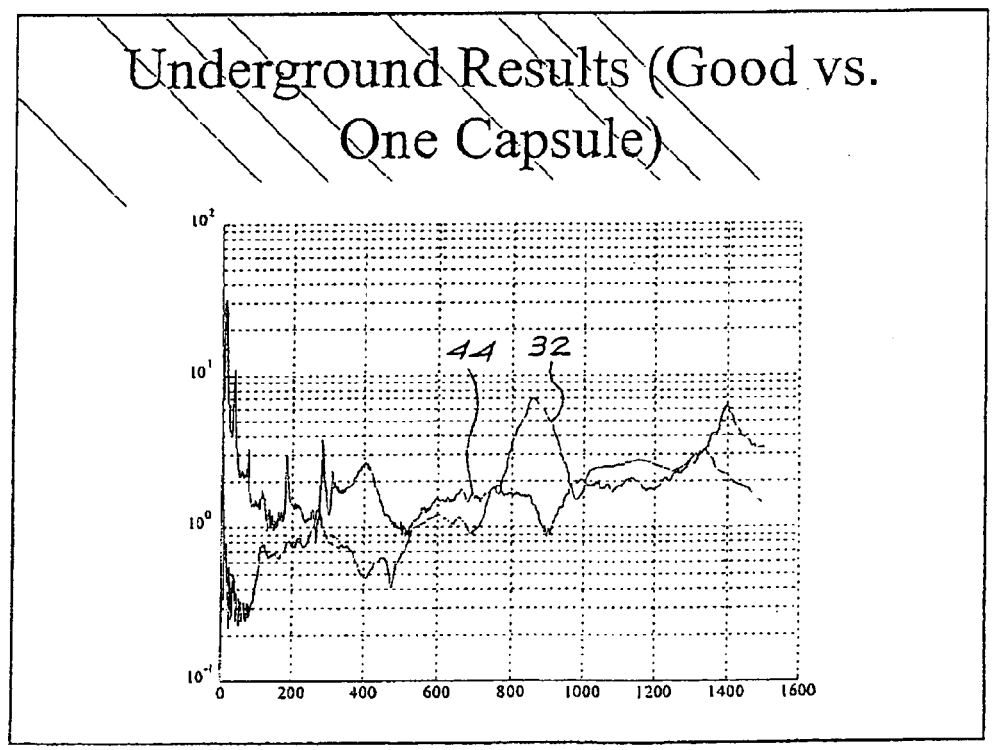

FIG. 13, which corresponds to a superimposition of FIGS. 4 and 6, shows the marked difference between the spectrum 32 and the spectrum 44 obtained for a bolt where the installation quality is poor as a result of the use of insufficient grout, i.e. use of one capsule of grout as opposed to the specified two capsules.

From the above it will be understood that where the installation quality of one response bolt is known it is possible to assess the installation quality of each of the other bolts in a test group by individually comparing the spectrum obtained for the good bolt with the spectra obtained for the other bolts. In this application of the invention, it is necessary to be able to identify one bolt for which the installation quality is good.

The periodic impacts may in some applications be applied at a predetermined frequency, for example 600 impacts/minute, but this is not necessary in all applications of the invention where multiple impacts are used.

The invention also envisages the possibility of assessing the overall installation quality of a group of bolts without having prior knowledge of which bolts in the group are of good installation quality. As before impacts are applied at a given frequency to a selected bolt in the group and the resulting signals are detected at each of the other bolts in the group. During analysis, comparisons are made between the frequency spectrum obtained for each bolt and for each other bolt in the group. In performing the analysis, use is made of a transfer or comparative function technique, as explained below with reference to FIGS. 14 and 15.

Figure 14:
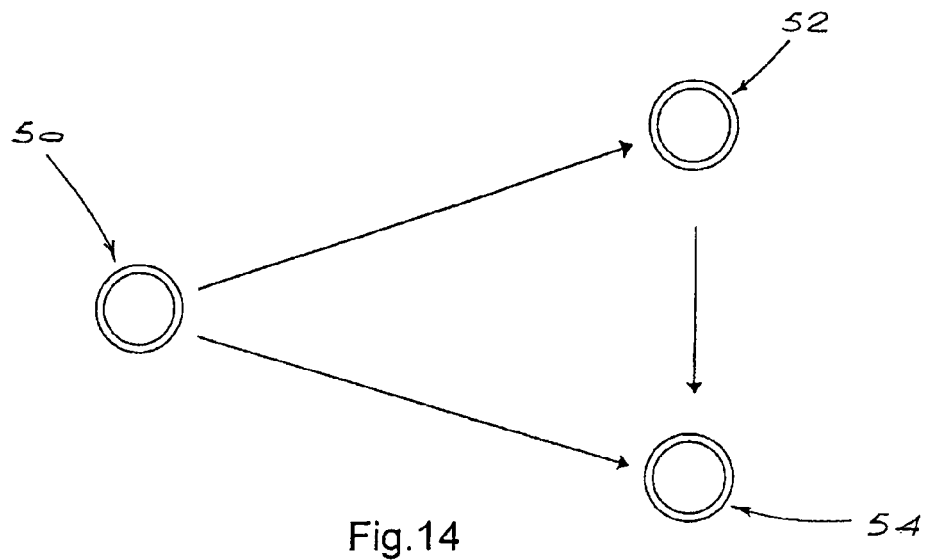
FIG. 14 diagrammatically illustrates, in a view similar to that of FIG. 2, an impact bolt and two response bolts.
Figure 15:
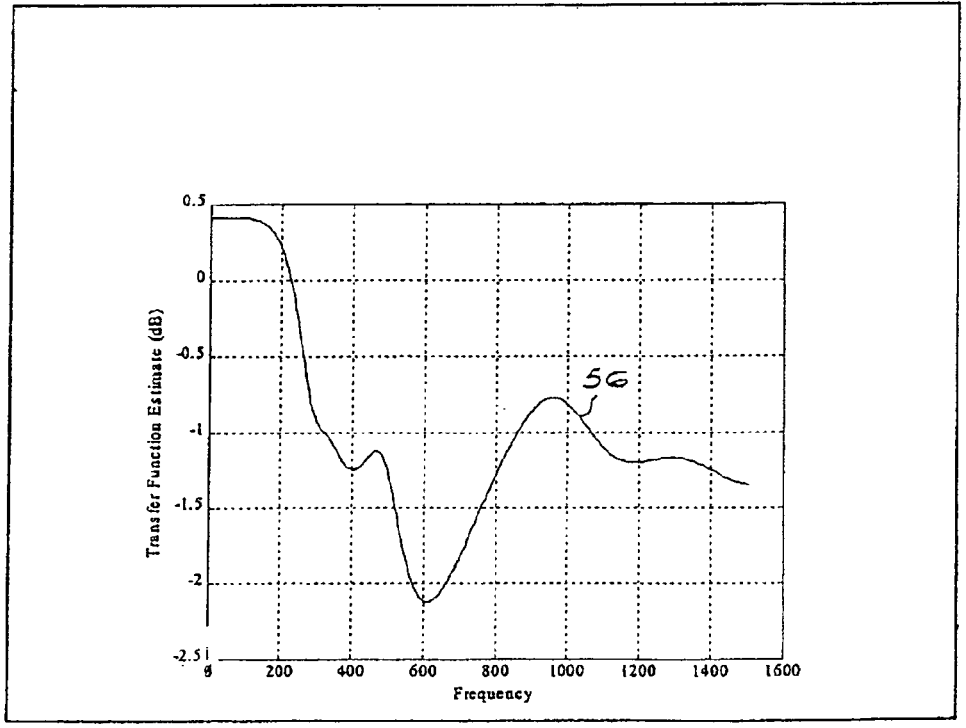
FIG. 15 graphically illustrates a transfer function obtained from a comparison of derived spectra for response bolts of good installation quality over a certain frequency range.

FIG. 14 diagrammatically illustrates a group of three bolts, being an impact bolt 50 and response bolts 52 and 54. Impacts are applied to the impact bolt as described above and the frequency spectra are obtained for the bolts 52 and 54 and are compared. If both bolts 52 and 54 are "good" bolts, i.e. they both enjoy good quality installation, their derived spectra will be similar to one another, i.e. will be largely equal to one another. In this case, the transfer function which must be applied to one spectrum to equalise it with the other spectrum will be approximately unity. This is exemplified in FIG. 15 which shows a calculated transfer or comparative function 56, ranging between +0.5 and −2 over the detected frequency range, for two "good" response bolts 52 and 54.

If the installation quality of both bolts is equally poor, the transfer or comparative function will again approximate to unity. Accordingly, if the comparison of the two spectra results in a calculated transfer function close to unity it can be assumed that both bolts are of equally good or equally bad installation quality.

Figure 16:
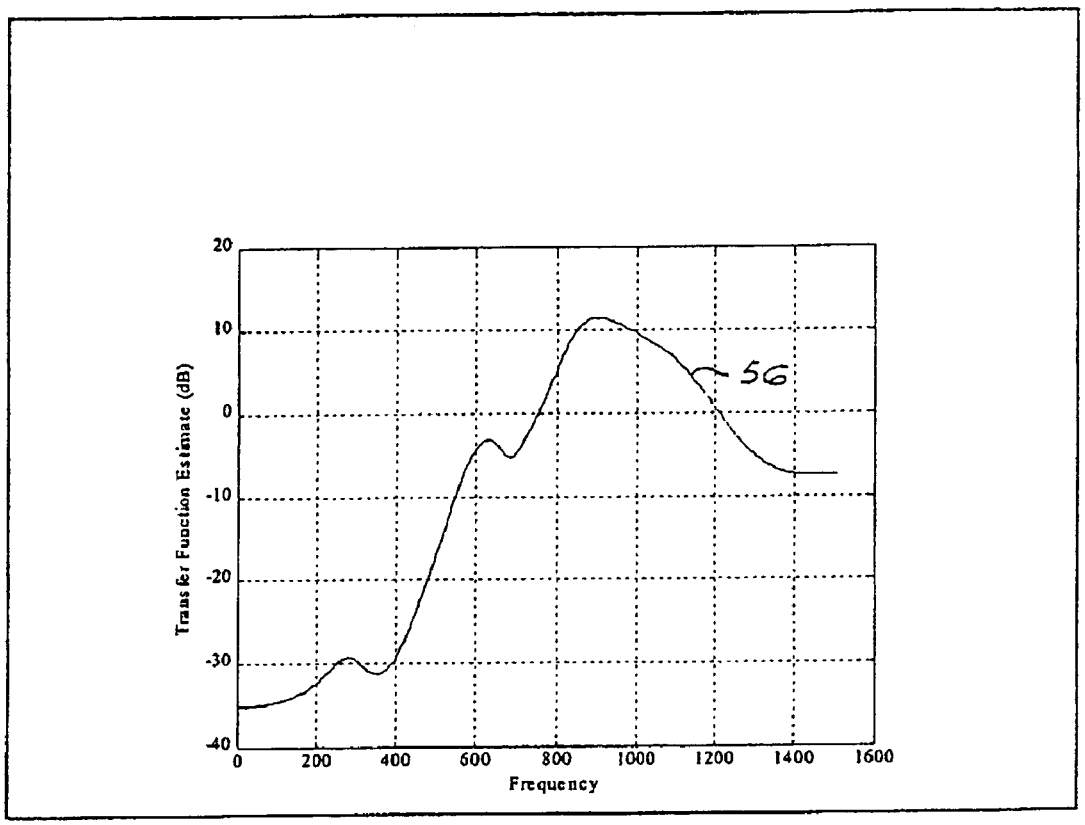
FIG. 16 shows a graph similar to that of FIG. 15 but for bolts of different installation quality.

If, on the other hand, the installation quality of one response bolt is substantially better than the installation quality of another response bolt, the calculated transfer or comparative function will not approximate to unity. This is exemplified in FIG. 16 where the transfer function 56 is seen to vary between +12 and −35 for the derived spectra for a "good" bolt and a "bad" bolt where the installation quality is poor as a result of use of insufficient grout.

From the totality of spectra derived from pairs of bolts, a matrix of transfer functions is built up. A statistical analysis of the total matrix gives an indication of the overall quality of installation of the group of bolts under consideration. For example, if the statistical analysis indicates that in a large number of cases, the quality of installation of bolts varies widely, i.e. the transfer functions vary widely from unity, this is an indication that the overall quality of installation of the bolt group is sub-standard.

It will be understood that in the absence of a derived spectrum for a bolt known to be a "good" bolt it is not possible in this application of the invention to assess accurately the installation quality of individual bolts in the group under test. However, the ability to assess the overall installation quality of a bolt group can be of major benefit to a mine operator in, say, a situation where the installation of roof bolts is contracted to a third party.

Using the technique described above, the mine operator can, for instance, determine whether the installation quality of a group of bolts installed by the contractor, seen as a whole, is acceptable in terms of the contract, or whether the group as a whole should be rejected and replaced by freshly installed bolts.

It is envisaged that the invention will have a number of benefits compared to conventional bolt testing techniques as described above.

In particular, a number of bolts can be tested simultaneously, in a relatively short period of time, using relatively unsophisticated equipment. When compared to techniques such as the "Boltometer" technique, the invention has the further advantage that no special preparation of the end of the bolt is required and, because the readings are taken at non-impacted bolts spaced from the impact bolt, the detection equipment does not have to be sufficiently robust to take impact forces.

As indicated previously, it is not necessary that the impact(s) be applied to the protruding end(s) of the tendon(s). It is envisaged that the principles of the invention will be equally applicable in situations where impact(s) are applied to another part of the system, for instance the rock or other mass in which the tendon(s) are grouted.

The invention also envisages that it will be possible to compare the response(s) of the tendon(s) with predetermined reference response(s) rather than with each other. In this situation it is envisaged that there will be a library of predetermined response(s) for different mass conditions, tendon lengths and so on with which a response obtained in situ can be compared, thereby to give an absolute evaluation of the installation quality of one or more tendons.

Alternatively, it is also within the scope of the invention, where multiple tendons are undergoing testing, to rank the bolts in order according to their installation quality and from such ranking determine which bolts have an adequate installation quality and which do not.

It will be understood that in many applications, the analysis which is carried out is a statistical analysis, and that such analysis may be carried out by an appropriately programmed computer. The computer may also be programmed to provide step-by-step, adaptive guidance to an operator implementing the technique or operating the apparatus of the invention.

Although the above detailed description refers to roof bolts it will be understood that that such bolts are not necessarily installed in a roof, but could also be installed in any rock or other surface.

We claim:

1. A method of testing the installation quality of a grouted anchor system, the system including a rock mass and a group of roof bolts each of which comprises a tendon anchored by grout in a hole in the rock mass, the method including the steps of:
   applying an acoustic signal to the system at a location spaced from the roof bolts of the group,
   detecting the acoustic responses of the roof bolts of the group to the applied signal,
   comparing the acoustic responses of roof bolts of the group with the acoustic responses of other roof bolts of the group in order to provide a plurality of response comparisons; and
   deducing the installation quality of the roof bolts of the group from the response comparisons.

2. A method according to claim 1 wherein the acoustic signal is applied by impacting the system.

3. A method according to claim 2 wherein a series of periodic impacts is applied to the system.

4. A method according to claim 3 wherein the impacts are applied to the system at a predetermined frequency.

5. A method according to claim 2 wherein the acoustic signal is applied by impacting a protruding end of a tendon of a roof bolt of the system which is not a roof bolt of the group.

6. A method according to claim 2 wherein the acoustic signal is applied by impacting the rock mass of the system.

7. A method according to claim 5 wherein the acoustic signal is applied by impacting the protruding end of a tendon of a roof bolt in respect of which grout installation quality is known to be good.

8. A method according to claim 1 wherein, for each comparison of one roof bolt response with another roof bolt response, a function is derived which can be applied to the one response to equalise it with the other response and the totality of the derived functions is analysed to give an indication of the installation quality of the roof bolts of the group as a whole.

9. Apparatus for testing the installation quality of a grouted anchor system, the system including a rock mass and a group of roof bolts each of which comprises a tendon anchored by grout in a hole in the rock mass, the apparatus including:
   means for applying an acoustic signal to the system at a location spaced from the roof bolts of the group,
   means for detecting the acoustic responses of the roof bolts of the group to the applied signal,
   means for comparing the acoustic responses of roof bolts of the group with the acoustic responses of other roof bolts of the group in order to provide a plurality of response comparisons from which the installation quality of the roof bolts of the group can be deduced.

10. Apparatus according to claim 9 comprising means for applying an acoustic signal to the system by impacting the system.

11. Apparatus according to claim 10 comprising means for applying a series of periodic impacts to the system.

12. Apparatus according to claim 11 comprising means for applying impacts to the system at a predetermined frequency.

13. Apparatus according to claim 9 comprising means for applying an acoustic signal to the system by impacting a protruding end of a roof bolt of the system which is not a roof bolt of the group.

14. Apparatus according to claim 9 comprising means for applying an acoustic signal to the system by impacting the rock mass.

15. Apparatus according to claim 9 comprising means for deriving, for each comparison of one roof bolt response with another roof bolt response, a function which can be applied to the one response to equalise it with the other response, and means for analysing the totality of the derived functions to give an indication of the installation quality of the roof bolts of the group as a whole.

* * * * *